United States Patent
Krenn

(10) Patent No.: US 12,311,806 B2
(45) Date of Patent: May 27, 2025

(54) INTERFACE DEVICE FOR A TRACK MAINTENANCE MACHINE

(71) Applicant: PLASSER & THEURER EXPORT VON BAHNBAUMASCHINEN GESELLSCHAFT M.B.H., Vienna (AT)

(72) Inventor: Stefan Krenn, Klaffer Am Hochficht (AT)

(73) Assignee: Plasser & Theurer Export von Bahnbaumaschinen Gesellschaft m.b.H., Vienna (AT)

( * ) Notice: Subject to any disclaimer, the term of this patent is extended or adjusted under 35 U.S.C. 154(b) by 1004 days.

(21) Appl. No.: 17/418,937

(22) PCT Filed: Nov. 28, 2019

(86) PCT No.: PCT/EP2019/082824
§ 371 (c)(1),
(2) Date: Jun. 28, 2021

(87) PCT Pub. No.: WO2020/135967
PCT Pub. Date: Jul. 2, 2020

(65) Prior Publication Data
US 2022/0105810 A1 Apr. 7, 2022

(30) Foreign Application Priority Data
Dec. 27, 2018 (AT) .................. A 389/2018

(51) Int. Cl.
*B60L 9/24* (2006.01)
*B60L 1/00* (2006.01)
*B60L 3/00* (2019.01)
*H02M 1/32* (2007.01)

(52) U.S. Cl.
CPC .................. *B60L 9/24* (2013.01); *B60L 1/20* (2013.01); *B60L 3/0023* (2013.01); *H02M 1/32* (2013.01); *B60L 2200/26* (2013.01); *B60L 2200/40* (2013.01)

(58) Field of Classification Search
CPC .. B60L 1/20; B60L 3/0023; B60L 9/24; B60L 2200/26; B60L 2200/40; H02M 1/32
See application file for complete search history.

(56) References Cited

U.S. PATENT DOCUMENTS 10,742,036 B2 8/2020 Rauma et al.
10,780,898 B2 9/2020 Greindl

FOREIGN PATENT DOCUMENTS

| CN | 207910551 U | 9/2018 |
| CN | 108736712 A | 11/2018 |
| EP | 2570292 A1 | 3/2013 |

(Continued)

Primary Examiner — Robert J McCarry, Jr.
(74) Attorney, Agent, or Firm — Laurence A. Greenberg; Werner H. Stemer; Ralph E. Locher

(57) ABSTRACT

An interface device for supplying a plurality of users with electrical power from a railway converter of a track maintenance machine includes a connection device for electrically linking to a DC voltage circuit of the railway converter and a distribution device, electrically connected to the connection device, for connecting the plurality users. A track maintenance system and a track maintenance machine are also provided.

12 Claims, 2 Drawing Sheets

(56) References Cited

FOREIGN PATENT DOCUMENTS

| | | | | |
|---|---|---|---|---|
| EP | 2629413 | A1 | 8/2013 | |
| EP | 3353348 | A1 | 8/2018 | |
| JP | 2014064398 | A * | 4/2014 | ................ B60L 9/30 |
| WO | 2018210533 | A1 | 11/2018 | |

* cited by examiner

INTERFACE DEVICE FOR A TRACK MAINTENANCE MACHINE

BACKGROUND OF THE INVENTION

Field of the Invention

The invention relates to an interface device for supplying several users with electrical power from a railway converter of a track maintenance machine. The invention further relates to a track maintenance system including an interface device of this kind. The invention additionally relates to a track maintenance machine having a track maintenance system of this type.

Description of the Related Art

Known from prior public use is a track maintenance machine having a rail car for travel on rails, a railway converter for supplying electrical power and several users for working on a track installation. For supply of the electrical power to the users, these are connected to an AC voltage circuit of the railway converter. By means of the railway converter, an overhead line voltage is converted first into a DC voltage and subsequently into the low voltage applied at the AC voltage circuit. It is disadvantageous that power losses occur during the conversion of the overhead line voltage into the DC voltage as well as during the conversion of the DC voltage into the AC voltage, resulting in noticeable losses of efficiency regarding the power supply to the users.

SUMMARY OF THE INVENTION

It is the object of the invention to provide an interface device for a track maintenance machine which ensures a particularly energy-efficient supply of electrical power to users.

This object is achieved by way of an interface device having the following features. According to the invention, it was recognized that an interface device for supplying several users with electrical power from a railway converter of a track maintenance machine, with a connection means for electrically linking to a DC voltage circuit of the railway converter and a distribution device for connecting the several users, guarantees a particularly energy-efficient supply of electrical power to the several users. Conventional railway converters comprise a railway rectifier for converting an AC current—applied at an overhead line or generated in a power generator—into a DC current, and a railway inverter for converting the DC current into an AC current for actuation of drive motors for displacing the track maintenance machine along rails, the drive motors being designed as asynchronous machines, for example. Converting electrical voltages is accompanied by power losses. The immediate connection of the interface device to the DC voltage circuit of the railway converter via the connection means advantageously ensures that power losses due to repeated conversions can be avoided. Preferably, only a single converter, in particular the railway rectifier, is arranged between the connection means and the overhead line, or between the connection means and the power generator, for converting or rectifying the AC voltage of the overhead line into a DC voltage of the DC voltage circuit. Overall, the interface device ensures a particularly efficient operation of the track maintenance machine as well as the economical production thereof.

According to one aspect of the invention, no other current converter is arranged between the railway rectifier and the users. The interface device can therefore be designed converter-less. Thus, the power supply of the users can take place in a particularly energy-efficient way.

Preferably, the interface device, in particular the connection means and/or the distribution device, is designed as a unit which is separate, in particular spatially, from the railway converter. Thus it is possible to avoid any intervention in the system of the railway converter which is subject to especially restrictive standards. Connecting the interface device to a railway converter, in particular an existing one, can thus take place in a simple manner.

The DC voltage circuit is also called DC intermediate circuit, since the same normally represents an intermediate circuit between the railway rectifier and the railway converter. For the functionality of the interface device, it is irrelevant whether or not a railway inverter is joined to the DC voltage circuit. It is essential that the interface device is designed for connection to the DC voltage circuit in order to avoid any power losses due to the repeated conversion on the part of the railway converter.

The interface device, in particular the connection means, is preferably designed for connection to a DC voltage circuit, the voltage of which is in a range of 200 V to 5.000 V, in particular from 350 V to 3.000 V, in particular from 500 V to 1.500 V, in particular from 600 V to 1.000 V. Preferably, the voltage applied at the DC voltage circuit is 750 V. An input voltage of the railway converter applied at the overhead line is preferably at least 5 kV, in particular at least 7.5 kV, in particular at least 10 kV, in particular at least 15 kV. The input voltage of the railway converter is preferably an AC voltage with an AC voltage frequency of 16⅔ Hz.

An interface device in which the connection means and the distribution device are connected to one another in an electrically conductive manner via a diode for directing electrical current from the connection means to the distribution device ensures a secure connection of the several users to the DC voltage circuit of the railway converter. The diode is designed for conducting current only in the direction from the connection means to the distribution device. The diode protects the railway converter from voltages which could react back from the users via the interface device to the railway converter. The railway converter is thus protected particularly securely from a damaging voltage increase on the side of the users.

An interface device having a smoothing unit for smoothing voltage fluctuations at the distribution device and/or at the connection means is particularly robust in operation and saves the railway converter and/or the several users from damage. Preferably, the connection means and the distribution device are connected to one another via the smoothing unit. The smoothing unit can be arranged in front of and/or behind the diode, as seen from the direction of the railway converter. The smoothing unit preferably comprises a throttle or an inductance, and/or a capacitor, and/or an ohmic resistor which is in particular adjustable. The smoothing unit can be designed for reducing brief voltage peaks. For damping an oscillating circuit, the smoothing unit can be designed such that voltage fluctuations are smoothed. The oscillating circuit comprises all the components connected to the interface device, in particular the users and the railway converter as well as the interface device itself. The smoothing unit can have a smoothing control unit for active damping of the oscillating circuit. This can be designed for controlling the adjustable resistor.

An interface device having an overvoltage protection for limiting a maximum voltage to a supply threshold voltage protects the railway converter and/or the several users from damaging overvoltage. The overvoltage protection is preferably arranged between the diode and the distribution device. The overvoltage protection preferably has a resistor for converting electric energy into thermal energy. The overvoltage protection can be designed for conducting current over the resistor if a voltage applied at the overvoltage protection and/or at the users exceeds the supply threshold voltage. Thus, electric energy can reliably be withdrawn from the power circuit, as a result of which any damage to the components connected to the power circuit can be avoided.

The overvoltage protection can be designed to switch into a TRIP state when the overvoltage occurs. In the TRIP state, a clocking of at least one of the converters, in particular the railway converter and/or the railway rectifier and/or an industrial converter, can be interrupted. Damage to the railway converter and/or the users by the overvoltage can thus be reliably avoided.

The overvoltage can have a switch, in particular a chopper, for in particular cyclic interruption of an electrically conductive connection. Further, the overvoltage protection can have a resistor for converting electric energy into thermal energy. Preferably, the overvoltage protection is designed so that an electrically conductive connection between the railway converter and the several users is interrupted when the supply threshold voltage is exceeded. For reducing electric energy, in particular for lowering the voltage applied at the overvoltage protection, the electric energy can be converted into thermal energy in the resistor. In particular, the overvoltage protection guarantees a protection of the power circuit which adjoins behind the diode, i.e. at the side of the distribution device.

An interface device in which the overvoltage protection is designed so that the supply threshold voltage is higher than a maximum voltage at the connection means which is limited by a railway overvoltage protection of the railway converter is particularly safe in operation and can be produced efficiently. Preferably, the supply threshold voltage is adapted to a maximum voltage of a railway overvoltage protection if such exists. The railway overvoltage protection is designed for limiting a voltage maximally applied at the DC voltage circuit and thus at the connection means. Such a railway overvoltage protection is commonly designed to be especially high-performance. The railway overvoltage protection can be further designed with the features of the overvoltage protection. In the case of a general voltage increase between the railway converter and the several users, as a result of the supply threshold voltage being set higher than the maximum voltage of the railway overvoltage protection, first the high-performance railway overvoltage protection is triggered and voltages are reduced. If there is a further voltage increase between the connection means and the several users, the overvoltage protection of the interface device is triggered. The overvoltage protection of the interface device can thus be produced to be especially small and efficiently. A reciprocal harmful interference of the overvoltage protection and the railway overvoltage protection can be reliably avoided.

It is a further object of the invention to provide a track maintenance system which can be operated in a particularly energy-efficient way and can be produced economically.

This object is achieved by way of a track maintenance system having an interface device according to the invention and at least one user connected to the interface device. The advantages of the track maintenance system according to the invention correspond to the advantages of the above-described interface device. Preferably, the at least one user is a user different from a motive drive, in particular the drive motor. The at least one user can have a user overvoltage protection. The user overvoltage protection can be further designed with the features of the overvoltage protection. In particular, the user overvoltage protection can be designed for reversibly interrupting an electrically conductive connection to the distribution device. In particular, the user overvoltage protection can be switchable into a TRIP state.

According to one aspect of the invention, the track maintenance system has at least two, in particular at least three, in particular at least four, in particular at least five, in particular at least ten users connected to the interface device.

A track maintenance system in which at least one of the users is designed for working on a track installation can be operated in a particularly energy-efficient manner. The track installation comprises rails, sleepers supporting the rails, a ballast bed and the overhead line. The at least one user for working on the track installation can be a tamping unit for consolidating the ballast bed and/or a rail layer for laying the rails and/or a crane for installing and maintaining the overhead line.

A track maintenance system in which at least one of the users is designed as an energy store is especially energy-efficient and can be operated in an economical manner. The energy store can be designed as an electro-chemical accumulator, in particular as a lithium-polymer accumulator, and/or as a capacitor and/or as a gyroscope. Thus, energy, in particular electrical energy, can be intermediately stored. For example, the track maintenance system can absorb into the energy store any energy which becomes available at short notice at the users, and release it again at a later point in time. The energy store can be dimensioned in such a way that it can supply at least one user with energy for several hours.

According to one aspect of the invention, the interface device has a recuperation unit for conducting energy, in particular electrical energy, from the at least one user to the energy store. In particular, energy becoming available at the at least one user during deceleration processes can thus be fed to the energy store and later be supplied to the users again and thus made use of.

According to a further aspect of the invention, at least one of the users comprises a fluid unit, in particular a hydraulic unit, having a fluid reservoir, in particular a hydraulic reservoir. The fluid reservoir is preferably designed for storing energy in the shape of fluid under pressure, in particular in the shape of hydraulic fluid or in the shape of pressurized air. Preferably, the recuperation unit is designed to conduct electrical energy from at least one of the users to the user with the fluid reservoir in order to store the same in the shape of fluidic energy. Surplus energy, in particular braking energy, can thus be used for charging the fluid store. Subsequently, this energy can be converted into motion energy in a fluidic drive, in particular a hydraulic drive. The storing of energy can thus be ensured particularly efficiently, in particular without the use of electro-chemical energy stores.

The recuperation unit can also be designed to supply the railway converter, in particular the railway inverter, with electrical energy from the energy store. To that end, the recuperation unit can be connected to the connection means in a current-conducting manner. For protecting the railway converter from overvoltage, the current-conducting connection is preferably switchable, i.e. reversibly severable. In particular, the switchable connection can be designed as a switchable bypass line which bridges the diode. Advantageously, this causes the railway converter to be protected from damaging voltage fluctuations on the part of the users, wherein a power supply of the at least one drive motor via the energy store is ensured.

A track maintenance system in which the at least one user has an industrial converter can be produced in a particularly economical way. As compared to the railway converter, an industrial converter is subject to fewer restrictions. No demands have to be made on the industrial converter to guarantee the continuity of the railway operation. An expensive verification record on default probabilities is for the most part not required with industrial converters. Industrial converters are thus significantly less expensive than railway converters with comparable characteristics. As opposed to industrial converters, railway converters are subject to the particularly restrictive requirements of the railway environment, in particular with regard to temperature range of application, shock resistance, vibration resistance, electromagnetic compatibility and fire safety. Typically, railway converters have a power input of at least 100 kW. The several users can have a power input of less than 100 kW. As a rule, railway converters are thus significantly more expensive than industrial converters. The at least one industrial converter is preferably connected to the distribution device and converts the supply DC voltage applied at the distribution device into a working voltage for a work drive. The working voltage can be a DC voltage or an AC voltage.

Preferably, the at least one industrial converter comprises a switch cabinet. The switch cabinet can have a damping support for mounting in a vibration-damping way. The switch cabinet can be designed to be fluid-tight, in particular liquid-tight. In addition, the switch cabinet can have a temperature monitor, in particular a temperature warning unit, for monitoring a temperature in the switch cabinet and/or for interrupting a power supply to the switch cabinet. Preferably, the switch cabinet has an air conditioning unit, in particular a cooling unit. The switch cabinet can have a fire protection unit, in particular an extinguishing unit.

According to one aspect of the invention, the industrial converter comprises redundant components. The industrial converter can have a switching unit for deactivating defective components and for activating functional components which are redundant to the defective components.

It is a further object of the invention to improve a track maintenance machine in such a way that it can be operated in a particularly energy-efficient manner and can be produced economically.

This object is achieved by way of a track maintenance machine having a rail car for riding on rails, a railway converter arranged on the rail car for providing electrical power and a track maintenance system, arranged on the rail car and connected to the railway converter, according to the invention. The advantages of the track maintenance machine according to the invention correspond to the advantages of the above-described track maintenance system and the above-described interface device. The railway converter comprises the railway rectifier for converting or rectifying an AC current applied, in particular, at the overhead line and/or at the current generator. Further, the railway converter can comprise the railway inverter connected to the railway rectifier for producing an AC voltage, in particular with variable frequency, and for actuating the drive motors for displacing the track maintenance machine along the rails. The power generator is powered in particular by a combustion engine. Arranged between the users and the overhead line and/or the power generator is preferably only a single converter, in particular the railway rectifier. Supplying the users with electrical power is thus particularly energy-efficient. By forgoing additional converters, the track maintenance machine can be produced in a particularly economical manner.

A track maintenance machine in which the railway converter has a DC voltage circuit to which the interface device is connected can be operated in a particularly energy-efficient manner. Preferably, the DC voltage circuit follows, in particular at the consumer side, a converter, in particular the railway rectifier, connected to the overhead line and/or the power generator.

A track maintenance machine in which a voltage of the DC voltage circuit is at most 5 kV can be operated in a particularly energy-efficient and economical manner. As a result of the voltage of the DC voltage circuit being at most 5 kV, in particular at most 3 kV, in particular at most 1.5 kV, in particular at most 1 kV, in particular at most 750 V, the at least one user, in particular the at least one user for working on the track installation and/or the at least one energy store, can be supplied directly with the voltage of the DC voltage circuit.

BRIEF DESCRIPTION OF THE DRAWINGS

Additional features, advantages and details of the invention become apparent from the following description of an embodiment. There is shown in.

DESCRIPTION OF THE EMBODIMENTS

Figure 1:
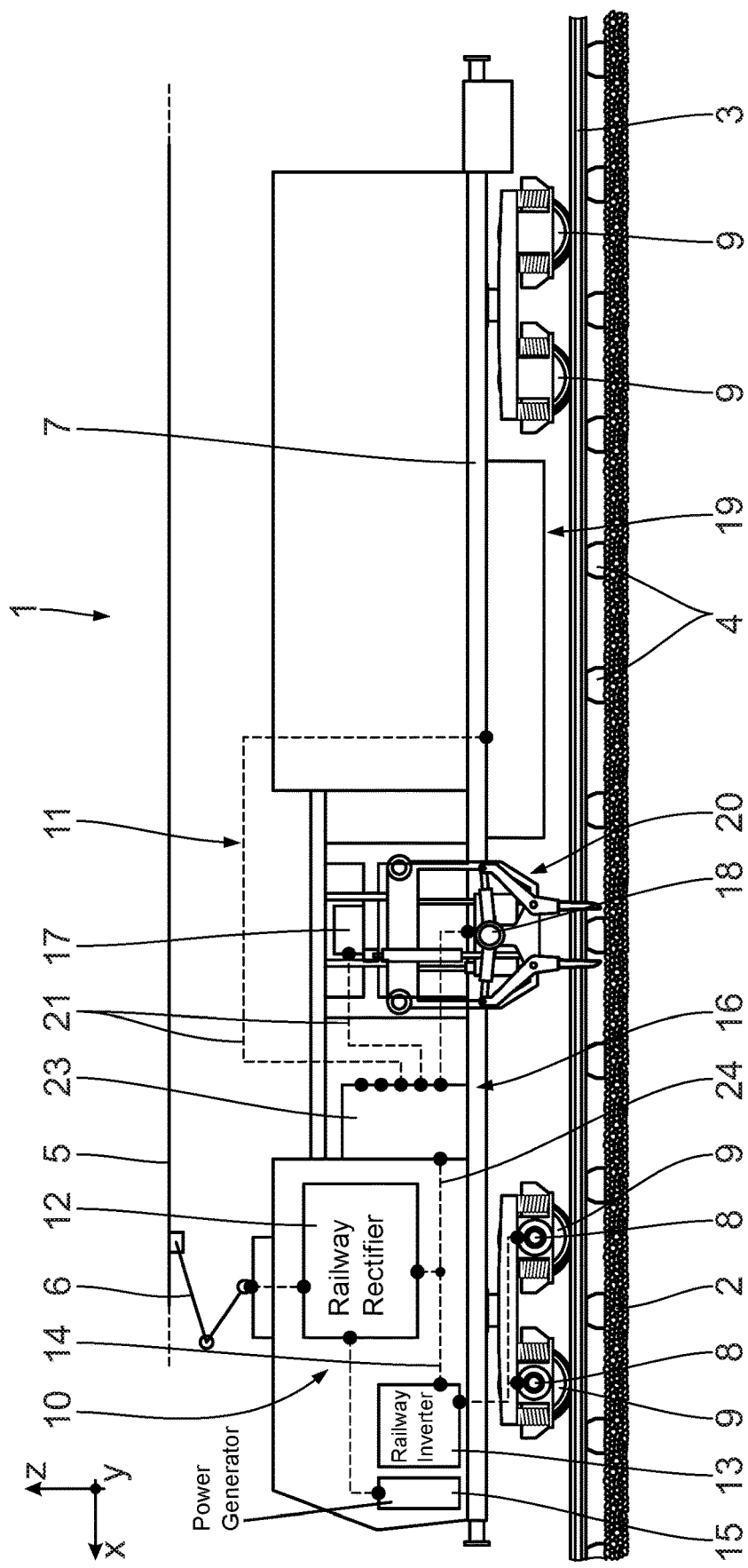
FIG. 1 a schematic representation of a track maintenance machine having a rail car, a railway converter arranged on the rail car, and a track maintenance system arranged on the rail car and connected to the railway converter, and FIG. 2 a schematic representation in detail of the railway converter and the track maintenance system in FIG. 1, wherein the track maintenance system has an interface device with a connection means and a distribution device.

Shown in FIG. 1 is a track maintenance machine 1 for working on a track installation, in particular for consolidating a ballast bed 2 of the track installation. The track installation comprises two rails 3 which rest on the ballast bed 2 via sleepers 4. The track installation further has an overhead line 5 for power supply of the track maintenance machine 1. The overhead line voltage provided at the overhead line 5 is 15 kV and has an overhead line frequency of 16⅔ Hz. The track maintenance machine 1 is in electrically conductive connection with the overhead line 5 via a pantograph 6.

The track maintenance machine 1 comprises a rail car 7 for travelling on the rails 3. The rail car 7 has drive motors 8 for displacing the track maintenance machine 1 on the rails 3. The drive motors 8 are in torque-transmitting connection to running wheels 9 of the rail car 7.

The track maintenance machine 1 has a railway converter 10 for supplying electrical power, in particular for converting the overhead line voltage into a converter DC voltage. In addition, the track maintenance machine 1 comprises a track maintenance system 11 arranged on the rail cars 7 and connected to the railway converter 10.

The railway converter 10 is electrically conductive connected to the pantograph 6. The railway converter 10 comprises a railway rectifier 12 for converting or rectifying the overhead line voltage into the converter DC voltage. The railway converter 10 further has a railway inverter 13. The railway inverter 13 is electrically conductive connected to the railway rectifier 12 via a DC voltage circuit 14. The converter DC voltage applied at the DC voltage circuit 14 is 750 V. The railway inverter 13 is designed for actuating the drive motors 8 with electrical power. For powering the drive motors 8 designed as three-phase induction machines, the railway inverter 13 supplies a drive AC voltage.

The track maintenance machine 1 additionally has a power generator 15, driven by a combustion engine, which is designed for supplying a generator voltage and is in electrically conducting connection to the railway rectifier 12. The power generator 15 allows the operation of the track maintenance machine 1 in the absence of an overhead line 5, or in the absence of actuation of the overhead line 5 with the overhead line voltage.

The track maintenance system 11 has an interface device 16 as well as several users 17, 18, 19 connected to the interface device 16. The users 17, 18 are designed for working on the track installation. The user 17 is a hydraulic drive of a tamping unit 20 of the track maintenance system 11. The user 18 is designed as an electrical eccentric drive of the tamping unit 20. The user 19 is an electro-chemical energy store, in particular a lithium-polymer accumulator. Present in each case between the users 17, 18, 19 and the interface device 16 is a current circuit called a user circuit 21. A consumer voltage applied at the user circuit 21 is 750 V.

Figure 2:
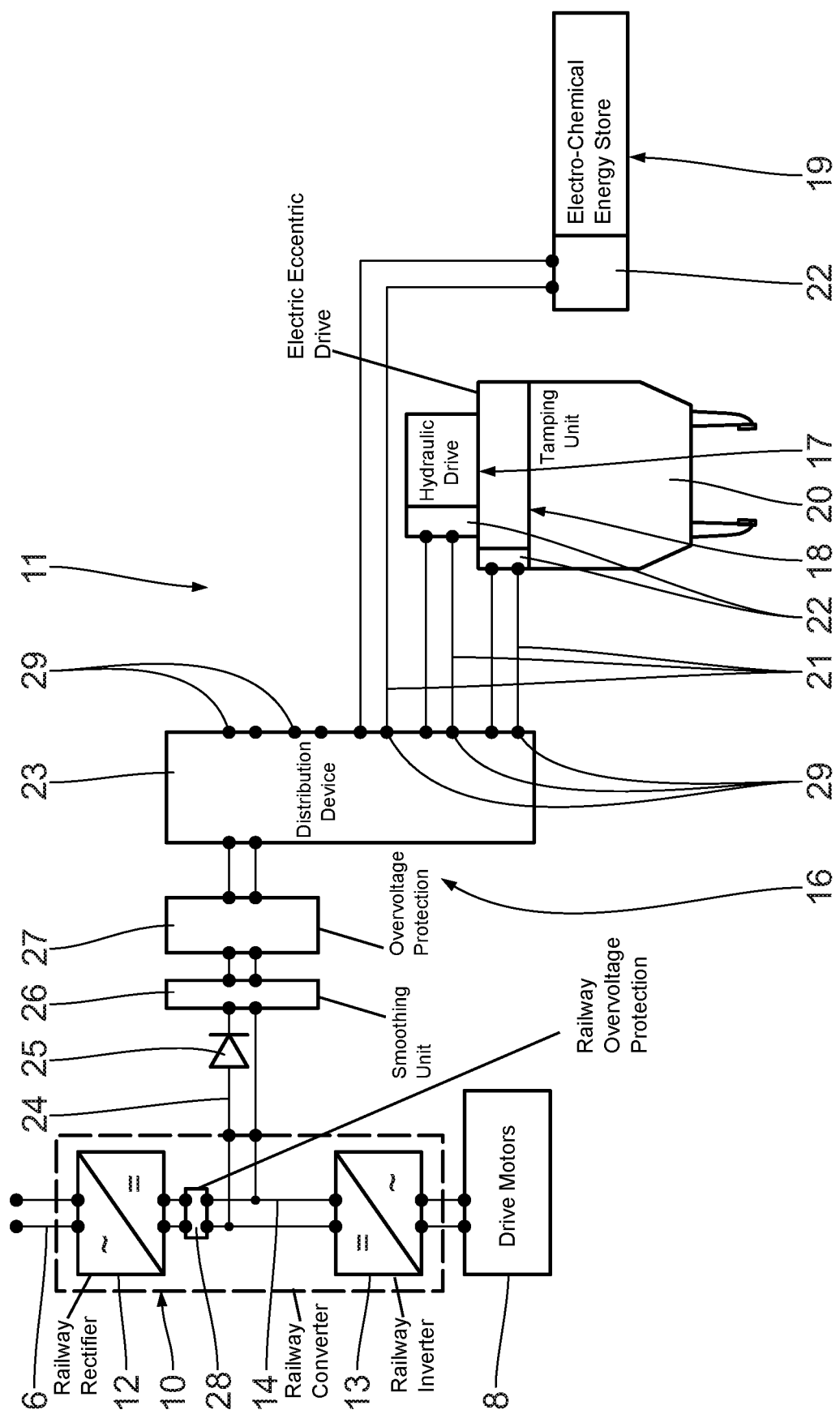

In FIG. 2, the railway converter 10 and the track maintenance system 11 are shown in further detail. The users 17, 18, 19 have industrial converters 22 for converting the user voltage present as DC voltage into the respectively required voltage form. The industrial converters 22 have an industrial overvoltage protection for interrupting a power supply if a threshold voltage is exceeded.

The interface device 16 has a distribution device 23 for electrical connection to the users 17, 18, 19. The interface device 16 further has a connection means 24 for electrically connecting the distribution device 23 to the railway converter 10, in particular to the DC voltage circuit 14.

The interface device 16 has a diode 25. Via the diode 25, the distribution device 23 is connected to the connection means 24. The diode 25 is designed for directing current from the connection means 24 to the distribution device 23. The diode 25 is designed as a semiconductor diode.

The interface device 16 has a smoothing unit 26 for smoothing voltage fluctuations at the distribution device 23, in particular between the diode 25 and the distribution device 23. For smoothing the voltage fluctuations, the smoothing unit 26 comprises a throttle, a capacitor and/or an ohmic resistor. The smoothing unit 26 is designed particularly for regulating or damping a possibly formed electrical oscillating circuit between the connection means 24 and the users 17, 18, 19 in such a way that voltage peaks are avoided.

The interface device 16 has an overvoltage protection 27. The overvoltage protection 27 is designed for limiting a maximum voltage at the distribution device 23 to a supply threshold voltage. The overvoltage protection 27 comprises a resistor for converting electric energy into thermal energy. The overvoltage protection 23 further comprises a chopper.

The railway converter 10 has a railway overvoltage protection 28. The railway overvoltage protection 28 is designed to limit the converter DC voltage to a converter threshold voltage. The overvoltage protection 27 is designed such that the supply threshold voltage is higher than the converter threshold voltage.

The mode of function of the track maintenance machine 1 or the track maintenance system 11 or the interface device 16 for supplying electrical power to the users 17, 18, 19 from the railway converter 10 is as follows:

The track maintenance machine 1 is situated on the rails 3 of the track installation. The pantograph 6 is in electrically conductive connection with the overhead line 5.

The track maintenance machine 1 is displaced along the rails 3. For that purpose, the overhead line voltage is converted into the converter DC voltage in the railway converter 10, in particular in the railway rectifier 12. The railway inverter 13 is supplied with electrical power via the DC voltage circuit 14 with the converter DC voltage. The railway inverter 13 converts the converter DC voltage into the drive AC voltage. The drive AC voltage supplied at the drive motors 8 causes the running wheels 9 to be driven. The track maintenance machine 1 is accelerated and displaced along the rails 3. The track maintenance machine 1 is displaced to that location where a treatment of the track installation, in particular a consolidation of the ballast bed 2, is to take place. The drive motors 8 are deactivated. To that end, a drive control interrupts the supply of drive AC voltage to the drive motors 8.

Electrical power is conducted via the connection means 24 to the diode 25. The diode 25 ensures a directed current conducting from the connection means 24 in the direction of the distribution device 23. The smoothing unit 26 connected in a current-conductive manner to the diode 25 smooths voltage peaks which result particularly from the rectifying in the railway rectifier 12. The voltage applied at the overvoltage protection 27 is less than the supply threshold voltage. The distribution device 23 is connected via the overvoltage protection 27 in a current-conductive way to the smoothing unit 26. The electrical power is conducted via the distribution device 23 via the user circuits 21 to the users 17, 18, 19.

A tamping unit control, not shown, controls the actuation of the hydraulic drive 17 and the eccentric drive 18 with electrical power. To operate a respective electric motor of the hydraulic drive 17 and the eccentric drive 18, the industrial converters 22 convert the supply DC voltage applied at the distribution device 23 into the required voltage form. Furthermore, the energy store 19 is charged via the industrial converter 22 and the user circuit 21. The ballast bed 2 is consolidated by means of the tamping unit 20.

Due to fluctuations of the overhead line voltage and/or based on a reaction of the drive motors 8, there may be voltage peaks in the DC voltage circuit 14. If a converter threshold voltage in the region of the DC voltage circuit 14 is exceeded, then the railway overvoltage protection 28 ensures a reduction of the converter threshold voltage. The railway overvoltage protection 28 converts electrical energy into thermal energy by means of a resistor. Surplus electrical energy is dissipated from the DC voltage circuit 14 in the shape of thermal energy.

An influence of voltage peaks on the DC voltage circuit 14 in the region of the user circuits 21 is prevented by the diode 25. If a voltage applied in the distribution device 23 exceeds the supply threshold voltage, electrical energy is converted into thermal energy by means of the overvoltage protection 27, in particular by means of the resistor, and is thus removed from the power circuit. The voltage in the power circuit is thus reliably lowered. Electrical energy is converted into thermal energy by means of a resistor of the overvoltage protection 27. A damage to the users 17, 18, 19, in particular the industrial converters, is thus reliably avoided.

In the case of an interruption of the energy supply via the DC voltage circuit 14, the energy store 19 can be used for supplying the users 17, 18. In particular, the energy store 19 can be used for supplying the users 17, 18 if there is no overhead line 5 available for supplying the track maintenance machine 1 with electrical power.

As a result of the interface device 16 being connected to the DC voltage circuit 14 of the railway converter 10, a supply of the users 17, 18, 19 with electrical power can take place in a particularly energy-efficient manner. Providing the supply threshold voltage at the users 17, 18, 19 dispenses with the intermediate step of inverting the supply DC voltage in the railway inverter 13 for supplying the users 17, 18, 19. Based on the avoidance of additional converters, the track maintenance system 11 can be produced particularly economically. Overall, the treatment of the track installation by means of the track maintenance machine 1 can take place in a particularly efficient and economical manner.

The invention claimed is:

1. An interface device for supplying a plurality users with electrical power from a railway converter of a track maintenance machine, the interface device comprising:
   a connection device for electrically linking to a DC voltage circuit of the railway converter; and
   a distribution device electrically connected to said connection device for connecting the plurality users;
   at least one of said connection device or said distribution device being a unit spaced apart from the railway converter and not being part of or integrated in the railway converter.

2. The interface device according to claim 1, which further comprises a diode electrically conductively interconnecting said connection device and said distribution device for directing electrical current from said connection device to said distribution device.

3. The interface device according to claim 1, which further comprises a smoothing unit for smoothing voltage fluctuations at least at one of said distribution device or said connection device.

4. The interface device according to claim 1, which further comprises an overvoltage protection for limiting a maximum voltage to a supply threshold voltage.

5. The interface device according to claim 4, wherein said overvoltage protection is configured to cause the supply threshold voltage to be higher than a maximum voltage at said connection device being limited by a railway overvoltage protection of the railway converter.

6. A track maintenance system, comprising:
   an interface device according to claim 1; and
   at least one user connected to said interface device.

7. The track maintenance system according to claim 6, wherein said at least one user is a plurality of users including at least one user configured for working on a track installation.

8. The track maintenance system according to claim 6, wherein said at least one user is a plurality of users including at least one user configured as an energy store.

9. The track maintenance system according to claim 6, wherein said at least one user is a plurality of users including at least one user having an industrial converter.

10. A track maintenance machine, comprising:
    a rail car for riding on rails;
    a railway converter disposed on said rail car for providing electrical power; and
    a track maintenance system disposed on said rail car and connected to said railway converter;
    said track maintenance system including an interface device according to claim 1 and at least one user connected to said interface device.

11. The track maintenance machine according to claim 10, wherein said railway converter has a DC voltage circuit to which said interface device is connected.

12. The track maintenance machine according to claim 11, wherein said DC voltage circuit has a voltage of at most 5 kV.

* * * * *